United States Patent
Freeman et al.

(10) Patent No.: US 6,491,721 B2
(45) Date of Patent: *Dec. 10, 2002

(54) TORIC INTRAOCULAR LENS MATERIAL

(75) Inventors: Charles Freeman, Arlington, TX (US); Mutlu Karakelle, Fort Worth, TX (US); Michael J. Simpson, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/761,070

(22) Filed: Jan. 16, 2001

(65) Prior Publication Data

US 2001/0014824 A1 Aug. 16, 2001

Related U.S. Application Data

(63) Continuation-in-part of application No. 09/728,681, filed on Dec. 1, 2000, which is a continuation-in-part of application No. 09/283,680, filed on Apr. 1, 1999, now abandoned.
(60) Provisional application No. 60/081,813, filed on Apr. 15, 1998.

(51) Int. Cl.[7] .................................................. A61F 2/16
(52) U.S. Cl. ...................................................... 623/6.56
(58) Field of Search .............................. 623/6.11, 6.56; 351/159

(56) References Cited

U.S. PATENT DOCUMENTS

| | | | |
|---|---|---|---|
| 4,179,484 A | 12/1979 | Neefe | 264/1 |
| 4,515,794 A | 5/1985 | Emery et al. | 514/249 |
| 4,680,998 A | 7/1987 | Council, Jr. | 82/1 |
| 4,725,276 A | 2/1988 | Bissonette et al. | 623/6 |
| 4,846,833 A | 7/1989 | Cumming | 623/6 |
| 4,918,165 A | 4/1990 | Soll et al. | 530/391 |
| 4,950,290 A | 8/1990 | Kamerling | 623/6 |
| 5,002,571 A | 3/1991 | O'Donnell, Jr. et al. | 623/6 |
| 5,078,740 A | 1/1992 | Walman | 623/36 |
| 5,290,892 A | 3/1994 | Namdaran et al. | 526/259 |
| 5,331,073 A | 7/1994 | Weinschenk, III et al. | 526/264 |
| 5,359,021 A | 10/1994 | Weinschenk, III et al. | 526/264 |
| 5,366,501 A | 11/1994 | Langerman | 623/6 |
| 5,370,687 A | 12/1994 | Poler | 623/6 |
| 5,375,611 A | 12/1994 | Lindqvist et al. | 128/898 |
| 5,405,385 A | 4/1995 | Heimke et al. | 623/6 |
| 5,549,670 A | 8/1996 | Young et al. | 623/6 |
| 5,576,345 A | 11/1996 | Mansson et al. | 514/449 |
| 5,593,438 A | 1/1997 | Akhavi et al. | 623/6 |
| 5,693,094 A | 12/1997 | Young et al. | 623/6 |
| 5,733,276 A | 3/1998 | Belkin | 606/6 |
| 5,796,462 A | 8/1998 | Roffman et al. | 351/161 |
| 5,805,260 A | 9/1998 | Roffman et al. | 351/161 |
| 6,027,531 A | 2/2000 | Tassignon | 623/6 |

FOREIGN PATENT DOCUMENTS

| | | |
|---|---|---|
| EP | 0 559 820 B1 | 9/1993 |
| EP | 0 904 747 A2 | 3/1999 |
| EP | 0 916 320 A2 | 5/1999 |
| WO | WO 94/11764 | 5/1994 |
| WO | WO 96/34629 | 11/1996 |
| WO | WO 98/15238 | 4/1998 |
| WO | WO 99/62435 | 12/1999 |
| WO | WO 00/26698 | 5/2000 |
| WO | WO 00/60383 | 10/2000 |

OTHER PUBLICATIONS

Boulton et al., "Adhesion of IOLs to the Posterior Capsule," British Journal of Ophthalmology, vol. 82(5); p. 468 (1998).
Cunanan et al., "An In Vitro Test Method to Study Posterior Capsular Opacification," Investigative Ophthalmology & Visual Science, vol. 38(4), p. S178 (1997).

(List continued on next page.)

Primary Examiner—Dinh X. Nguyen
(74) Attorney, Agent, or Firm—Patrick M. Ryan

(57) ABSTRACT

A method of selecting an intraocular lens material for toric lenses is disclosed. The method comprises determining the tack of the material.

8 Claims, 1 Drawing Sheet

OTHER PUBLICATIONS

Gabriel et al., "In Vitro Adherence of *Pseudomonas aeruginosa* to Four Intraocular Lenses," *J. Cataract Refractive Surg*, vol. 24, pp. 124–129 (1998).

Grabow et al., "Toric Intaocular Lens Report," *Annals of Ophthalmology*, vol. 29(3), pp. 161–163 (1997).

Hollick et al., "Lens Epithelial Cells Regression on the Posterior Capsule: A 2 Year Prospective, Randomised Trial With Three Different IOL Materials," *Investigative Ophthalmology & Visual Science*, vol. 38(4), p. S19 (1997).

Johnston et al., "In Vitro Protein Adsorption to 2 Intraocular Lens Materials," *J. Cataract & Refractive Surgery*, vol. 25, pp. 1109–1115 (1999).

Kanagawa et al., "Presence and distribution of fibronectin on the surface of implanted intraocular lenses in rabbits," *Graefe's Archive for Clinical & Exp. Ophthalmology*, vol. 228, pp. 398–400 (1990).

Linnola et al., "Acrylate Intraocular Lenses (IOLs) Hinder Posterior Migration of Epithelium; Activity Tested by Corneal Tissue Cultures," *ESCRS Abstracts*, p. 120 (1997).

Linnola et al., "Adhesion of soluble fibronectin, laminin, and collagen type IV to intraocular lens materials," *J. of Cataract & Refractive Surgery*, vol. 25 (11), pp. 1486–1491 (1999).

Linnola et al., "Intraocular lens bioactivity tested using rabbit corneal tissue cultures," *J. Cataract & Refractive Surgery*, vol. 25, pp. 1480–1485 (1999).

Linnola, "Sandwich Theory: Bioactivity–based Explanation for Posterior Capsule Opacification," *J. Cataract Refract. Surg.*, vol. 23, pp. 1539–1542 (1997).

Liu et al., "A Study of Human Lens Cell Growth In Vitro," *Investigative Oph. & Visual Science*, vol. 37(5), pp. 906–914 (1996).

Mandle, "Acrylic Lenses Cause Less Posterior Capsule Opacification than PMMA, Silicone IOLs," *Ocular Surgery News*, vol. 14(15) (1996).

Nagamoto et al., "Effect of Intraocular Lens Design on Migration of Lens Epithelial Cells Onto the Posterior Capsule," *J. Cataract Refract Surg.*, vol. 23, pp. 866–872 (1997).

Nagata et al., "Adhesiveness of AcrySof to a Collagen Film," *J. Cataract Refract. Surg.*, vol. 24, pp. 367–370 (1998).

Nagata et al., "Optic Sharp Edge or Convexity: Comparison of Effects of Posterior Capsular Opacification," *Jpn J. Ophthal.*, vol. 40, pp. 397–403 (1996).

Nguyen et al., "Digital Overlay Technique for Documenting Toric Intraocular Lens Axis Orientation," *J. Cataract Refractive Surgery*, vol. 26, pp. 1496–1504 (2000).

Nishi et al., Inhibition of Migrating Lens Epithelial Cells By Blocking The Adhesion Molecule Integrin: A Preliminary Report, *J. Cataract Refract. Surg*, vol. 23 (1997).

Oshika et al., "Adhesion of Lens Capsule to Intraocular Lenses of Polymethylmethacrylate, Silicone and Acrylic Foldable Materials: An Experimental Study," *British Journal of Ophthalmology*, vol. 82, pp. 549–553 (1998).

Oshika et al., "Incision/Phacoemulsification," Symposium on Cataract, IOL and Refractive Surgery, Jun., 1996.

Oshika et al., "Two Year Clinical Study of a Soft Acrylic Intraocular Lens," *J. Cataract Refract. Sur.*, vol. 22, pp. 104–109 (1996).

Pande et al., "High–Resolution Digital Retroillumination Imaging of the Posterior Lens Capsule After Cataract Surgery," *J. Cataract Refract. Surg.*, vol. 23, pp. 1521–1527 (1997).

Pande et al., "Posterior Capsular Opacfication With PMMA, Silicone and Acrysof Intraocular Lenses: A Prospective Randomized Clinical Trial," *Investigative Ophthalmology & Visual Science*, vol. 36(4), p. S397 (1995).

Patel et al., "Postoperative Intraocular Lens Rotation," *Ophthalmology*, vol. 106(11), pp. 2190–2196 (1999).

Reich et al., "Intraocular–Lens–Endothelial Interface: Adhesive Force Measurements," *J. of Biomedical Materials Research*, vol. 187, pp. 737–744 (1984).

Ruhswurm et al., "Astigmatism Correction With a Foldable Toric Intraocular Lens in Cataract Patients," *J. Cataract Refractive Surgery*, vol. 26, pp. 1022–1027.

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Sun et al., "Toric Intraocular Lenses for Correcting Astigmatism in 130 Eyes," *Ophthalmology*, vol. 107(9), pp. 1776–1782.

Ursell et al., Anterior Capsule Stability in Eyes With Intraocular Lenses Made of Poly(methyl methacrylate), Silicone, and AcrySof, *J. Cataract Refractive Surg.*, vol. 23, pp. 1532–1538 (1997).

Ursell et al., "Relationship Between Intraocular Lens Biomaterials and Posterior Capsule Opacification," *J. Cataract Refractive Surg.* vol. 24, pp. 352–360 (1998).

Ursell et al., "The In Vivo Movement of Cells on the Surface of Intraocular Lenses in Humans Observed with Sequential Specular Photomicrography," *Investigative Ophthalmology & Visual Science*, vol. 36(4), S795 (1995).

Werner et al., "Endothelial Damage Caused by Uncoated and Fluorocarbon–Coated Poly(methyl methacrylate) Intraocular Lenses," *J. Cataract Refractive Surgery*, vol. 23, pp. 1013–1019 (1997).

Yang et al., "Membrane Formation and Cellular Response on the Surface of Lenses Implanted in Rabbit Eyes," *J. Cataract Refractive Surg.*, vol. 23, pp. 1265–1270 (1997).

TORIC INTRAOCULAR LENS MATERIAL

This application is a continuation-in-part application of U.S. patent application Ser. No. 09/728,681, filed Dec. 1, 2000, which is a continuation-in-part application of U.S. patent application Ser. No. 09/283,680, filed Apr. 1, 1999, now abandoned, which claims priority from U.S. Provisional Patent Application Ser. No. 60/081,813, filed Apr. 15, 1998.

FIELD OF THE INVENTION

This invention relates to intraocular lenses. In particular, the present invention relates to toric intraocular lenses.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, *Foldable Intraocular Lenses,* Ed. Martin et al., Slack Incorporated, Thorofare, N.J. (1993). Biocompatibility varies among different IOL materials within and among each category.

One measure of biocompatibility for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15 (1996). See, also, Oshika, et al., "Two Year Clinical Study of a Soft Acrylic Intraocular Lens," J. Cataract. Refract. Surg., 22:104–109 (1996); and Ursell et al., "Relationship Between Intraocular Lens Biomaterials and Posterior Capsule Opacification," J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. Nos. 5,576,345 (pharmaceutical agent=the cytotoxic agent taxol or an ophthalmically acceptable derivative); 4,515,794; and 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts." Yet another method involves the physical destruction or removal of lens epithelial cells. See, Saika et al., J. Cataract Refract. Surg., 23:1528–1531 (1997).

Another method of addressing PCO is the prophylactic laser therapy method disclosed in U.S. Pat. No. 5,733,276. According to this method, the lens capsule is irradiated with laser irradiation to destroy cells that remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment-preventing compound onto the posterior surface of the lens capsule. The stable or permanent layer may be a polymer, such as polyethylene glycol, polysaccharides, polyethylenepropylene glycol, and polyvinyl alcohol.

Aside from biocompatibility concerns, positional stability after implantation is a very important concern for toric IOLs. Toric IOLs are designed to be oriented in a specific way in order to provide the desired vision correction. These IOLs should not rotate or slip from their implanted position.

SUMMARY OF THE INVENTION

The present invention relates to a method of selecting an IOL material for reducing the risk of posterior capsule opacification. IOL materials having a certain tack are more likely to reduce the risk of posterior capsule opacification than are materials having a lower tack. Tack is determined by measuring the maximum load required to separate two pieces of the same material.

The present invention also relates to a method of selecting a material for toric IOLs. IOL materials having a certain tack allow implanted toric IOLs to remain in their intended position and provide their designed correction.

DETAILED DESCRIPTION OF THE INVENTION

According to the present invention, IOL optic materials are selected based on their tack. Tack is the maximum load required to separate two pieces of the same material that have been placed in contact with each other. The maximum load required to separate two pieces of the same material varies with a number of factors, including the contact surface area, the shape of the material samples, the length of time the materials are held in contact with each other prior to separation and the weight, if any, placed on the materials after they are contacted with each other.

IOL materials having a tack greater than that of an IOL material consisting of 65% (w/w) 2-phenylethyl acrylate, 30% (w/w) 2-phenylethyl methacrylate, 3.2% (w/w) 1,4-butanediol diacrylate and 1.8% (w/w) 2-(2"-hydroxy-3'-methallyl-5'-methylphenyl)benzotriazole, wherein this IOL material has been cured at 80° C. for 2 hours, then 100° C. for 2 hours using 1% (w/w) di-(4-t-butylcyclohexyl) peroxydicarbonate as a polymerization initiator, reduce the risk of posterior capsule opacification when implanted into the human lens capsule. To determine the tack of an IOL material ("test material") and compare it to that of the IOL material specified immediately above ("standard material"), all that is necessary is that both the test material and standard material be of the same size and shape and the testing parameters be identical. The standard material does not have to be exactly the material defined above, but can be any material having an equivalent tack. The ratio of the tack of the test material to that of the standard material is defined as the "Tack Quotient." According to the present invention, IOL materials are selected that have a Tack Quotient of 1 or greater, provided that the IOL material does not consist essentially of (i) 2-phenylethyl acrylate and 2-phenylethylmethacrylate or (ii) ethyl acrylate, ethyl methacrylate and trifluoroethylmethacrylate. IOL materials having a Tack Quotient higher than about 3 generally present handling problems that may make them unsuitable for use as a foldable IOL material. The IOL materials are preferably chosen so that they have a Tack Quotient of about 1–2, and more preferably about 1–1.5.

Figure 1:
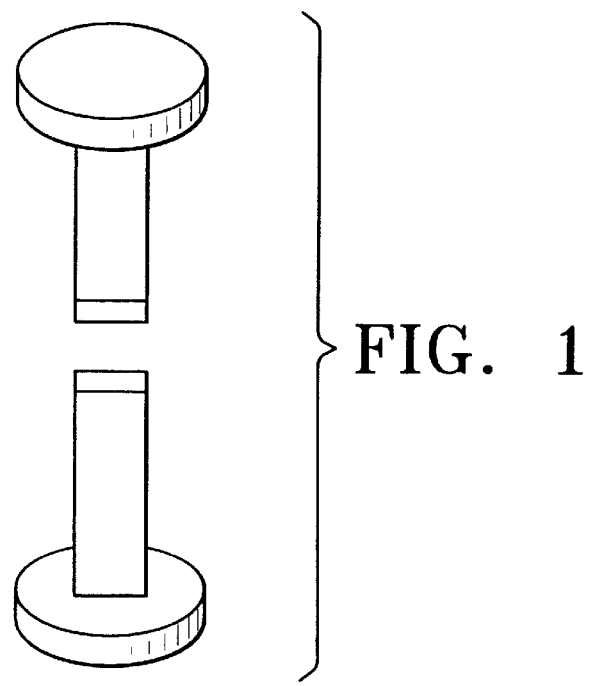
FIG. 1 illustrates a T-shaped post.

A preferred method of measuring tack is as follows. Two 6-mm diameter, 1-mm thick flat disks of an IOL material are prepared ("Test Disks"). Each Test Disk is then secured to the flat surface of a T-shaped post adapted for use with the tensile testing machine. For example, the T-shaped posts can be made of polycarbonate materials and have the shape shown in FIG. 1. The Test Disks are secured to the T-shaped posts using any glue that does not imbibe into the lens material, swelling it and changing the material's surface properties. The glue is preferably a quick-setting glue so that minimal penetration is allowed. In the case of foldable acrylic IOL materials, such as those described in U.S. Pat. Nos. 5,290,892 and 5,693,095, suitable glues include epoxy resins. The glue should be chosen and used in an amount such that the Test Disks do not separate from the T-shaped posts during the tack test.

Figure 2:
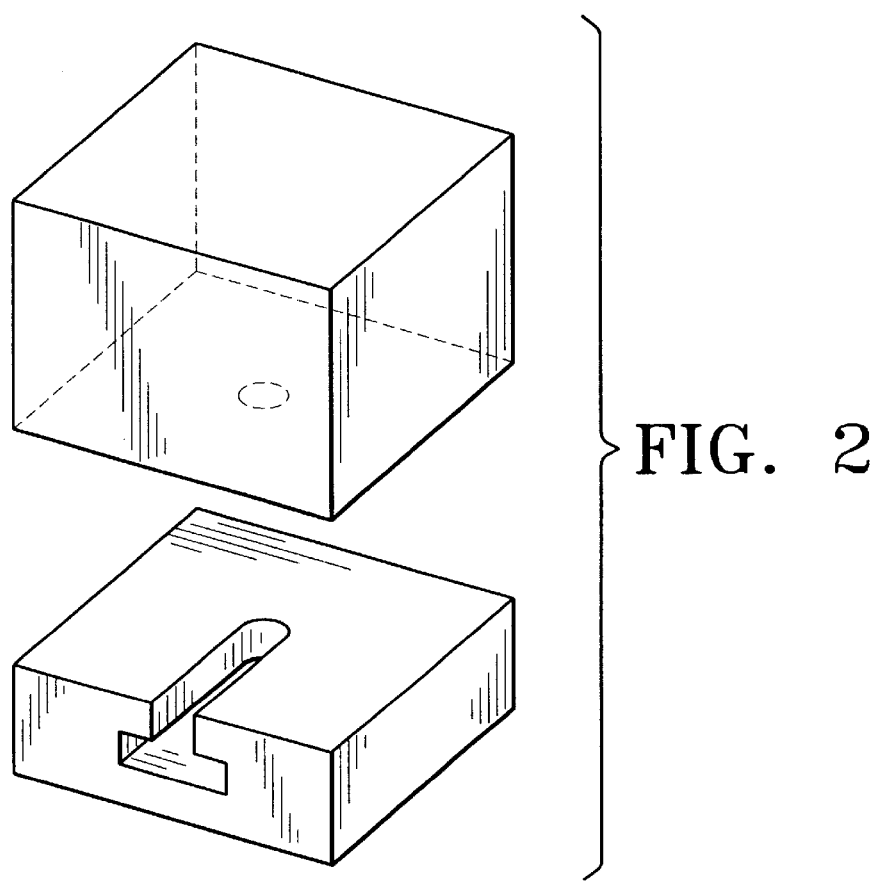
FIG. 2 illustrates an assembly for holding a T-shaped post.

Once the Test Disks are secured to the T-shaped posts, the glue should be allowed to dry thoroughly. In the case of epoxy resins, the drying time could be approximately 15 hours or so. After the glue has thoroughly dried, the Test Disks are placed in contact with each other, under an appropriate weight, preferably a weight of about 200 g. The Test Disks are held in contact with each other for approximately two minutes, after which time the weight is removed and the maximum load required to separate the Test Disks is measured by pulling the Test Disks apart using a crosshead speed of about 1 mm/min. In a preferred embodiment, the tensile testing machine's assembly for holding the T-shaped posts is configured to allow a weight to rest on the bottom of an inverted T-shaped post, as shown in FIG. 2. This test is preferably conducted at ambient conditions, with n=3–6. The tensile testing machine pulls the T-shaped posts away from each other until separation. The maximum load recorded prior to separation is the tack. For example, the tensile testing machine can be an Instron Material Tester (Model No. 4442 or equivalent). Maximum load is can be expressed in a number of ways, including being expressed in Newtons.

Although the method of the present invention could be applied to silicone and hydrogel IOL materials, such materials are generally not tacky to the extent that only a minimal load, if any, is required to separate them from themselves. The method of the present invention is preferably used to select IOL materials from the family of ophthalmically acceptable foldable acrylic materials. Most preferred are the foldable acrylic materials comprising one or more monomers of the formula

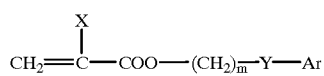

(I)

wherein:
X is H or $CH_3$;
m is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

Monomers of Formula I are known and include, but are not limited to: 2-phenoxyethyl acrylate; 2-phenylethylthio acrylate; 2-phenylethylamino acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; and their corresponding methacrylate compounds. These acrylic/methacrylic monomers and others are disclosed in U.S. Pat. No. 5,290,892, the entire contents of which are hereby incorporated by reference. Suitable IOL materials for screening using the method of the present invention also include, but are not limited to, those disclosed in U.S. Pat. No. 5,331,073, the entire contents of which are hereby incorporated by reference.

Preferred monomers of Formula I are those where m is 2–4; Y is nothing or O; and Ar is phenyl. Most preferred are 2-phenylethyl acrylate; 2-phenoxyethyl acrylate; 3-phenylpropyl acrylate; 3-phenoxypropyl acrylate; 4-phenylbutyl acrylate; 4-phenoxybutyl acrylate; and their corresponding methacrylate compounds.

Using the preferred method of testing tack described above and an Instron Materials Tester Model No. 4442, the following results are obtained:

1. IOL material=78 wt. % 2-phenylethyl acrylate; 18 wt. % 2-phenylethyl methacrylate; 2 wt. % of 1,4-butanediol diacrylate; 1 wt. % 2-(2'-hydroxy-3'-methallyl-5'-methyl phenyl) benzotriazole; and 1 wt. % of di-(tert-butylcyclohexyl) peroxydicarbonate. Results (max. load, N)=approx. 7–8±1.2.

2. IOL material=74.2 wt. % 2-phenylethyl acrylate; 16.8 wt. % 2-phenylethyl methacrylate; 5 wt. % N-vinyl pyrrolidone; 2 wt. % of 1,4-butanediol diacrylate; 1 wt. % 2-(2'-hydroxy-3'-methallyl-5'-methyl phenyl) benzotriazole; and 1 wt. % of di-(tert-butylcyclohexyl) peroxydicarbonate. Results (max. load, N)=approx. 13.4±2.4.

3. IOL material=74.1 wt. % 2-phenylethyl acrylate; 6.9 wt. % 2-phenylethyl methacrylate; 15 wt. % polyethylene oxide (wt. avg. molecular weight of 1000) dimethacrylate; 2 wt. % of 1,4-butanediol diacrylate; 1 wt. % 2-(2'-hydroxy-3'-methallyl-5'-methyl phenyl) benzotriazole; and 1 wt. % of di-(tert-butylcyclohexyl) peroxydicarbonate. Results (max load, N)=approx. 0.

Preferably, IOL materials are also substantially free of glistenings in a physiologic environment and for which the amount of collagen IV that remains adhered to the material in step (d) is about 30–100% of the amount that remains adhered in step (b). Glistenings are the result of condensation of water vapor within the lens. Although glistenings have no detrimental effect on the function or performance of IOLs made from acrylic materials, it is nevertheless cosmetically desirable to minimize or eliminate them. IOL materials are substantially free of glistenings in a physiologic environment if they have an average of no more than approximately 1–2 glistenings per $mm^2$ when evaluated in the test described below. Preferably, the average number of glistenings per $mm^2$ will be much less than 1.

The presence of glistenings is measured by placement of a lens sample into a vial and adding deionized water or a balanced salt solution. The vial is then placed into a water bath preheated to 45° C. Samples are to be maintained in the bath for 24 hours. The sample is then placed either in a 37° C. bath or at room temperature and allowed to equilibrate for 2 hours. The sample is removed from the vial and placed on a microscope slide. Visualization of glistenings is done with light microscopy using a magnification of 50 to 200x.

Furthermore, IOL materials are preferably selected so that they possess the following refractive index, $T_g$, and elongation properties, which make the materials particularly suitable for use in IOLs which are to be inserted through incisions of 5 mm or less.

The IOL material preferably has a refractive index of at least about 1.50 as measured by an Abbe' refractometer at 589 nm (Na light source). IOL optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the IOL material, which affects the material's folding and unfolding characteristics, is preferably between about −20 to +25° C., and more preferably between about −5 and +16° C. Tg is measured by differential scanning calorimetry at 10° C./min., and is determined at the midpoint of the transition of the heat flux curve.

The IOL material should also have an elongation of at least about 150%, preferably at least 200%, and most preferably about 300–600%. This property indicates that an IOL optic made of the material generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance.

Implantable toric IOLs are designed to correct pre-existing corneal astigmatism, typically in patients undergoing cataract surgery. Toric IOLs have one surface (posterior or anterior) that contains a first radius of curvature at one meridian and a second radius of curvature at a second meridian perpendicular to the first. The axis of toric correction on the IOL must be aligned correctly with the astigmatic axis of the corneal astigmatism for optimal results.

IOLs are commonly implanted in the capsular bag after the cataractous lens is removed. Toric IOLs must remain in a specific orientation within the eye in order to achieve the designed correction. Rotation after implantation is a significant concern with toric IOLs. See, for example, Sun et al., Ophthalmology, 107(9):1776–1782 (2000); Patel et al., Ophthalmology, 106(11):2190–2196 (1999); Nguyen, et al., J. Cataract Refract. Surg., 26:1496–1504 (2000); and Ruhswurm, et al., J. Cataract Refract. Surg., 26:1022–1027 (2000).

Toric IOLs made of materials that have insufficient tack can rotate, slip and/or become "decentered" over time due to a variety of factors including capsular fibrosis, wound healing, and, particularly in the case of undersized lenses, normal movement of the eye. Single- and multi-piece toric IOLs of conventional designs made of materials selected according to the present invention will remain in their intended position when implanted in the capsular bag, rotating less than 10°. In the case of multi-piece designs, it is not necessary for both the optic and haptic(s) to consist solely of materials selected according to the present invention. Preferably, at least the optic consists of materials selected according to the present invention, though IOLs where only the haptic(s) consist of materials selected according to the present invention are also within the scope of the present invention. Toric IOLs made of other materials but having the optic's anterior surface, posterior surface, or both, coated with materials selected according to the present invention also will remain in their intended position, rotating less than 10°, and are within the scope of the present invention. Likewise, toric IOLs made of other materials but having the haptic(s) coated with materials selected according to the present invention will remain in their intended position, rotating less than 10°, and are within the scope of the present invention.

Thus, in one embodiment, the present invention relates to toric intraocular lenses comprising an optic having an anterior surface, posterior surface, or both, consisting of (i.e., coated with) a material that has a Tack Quotient of about 1 or greater, provided that said material does not consist essentially of (i) 2-phenylethyl acrylate and 2-phenylethylmethacrylate or (ii) ethyl acrylate, ethyl methacrylate and trifluoroethylmethacrylate. In this embodiment, where the materials of the present invention form a coating on the optic, the coating should be of uniform thickness. In another embodiment, the optic does not comprise materials selected according to the method of the present invention, but the haptic(s) are coated with materials selected according to the present invention. Coatings can be applied using known techniques, including solution and vapor deposition techniques. The coating, whether on the optic or haptic(s), generally will be about 25 μm or less in thickness.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A toric intraocular lens comprising an optic having an anterior surface, posterior surface, or both, consisting of a material that has a Tack Quotient of about 1 or greater, provided that said material does not consist essentially of (i) 2-phenylethyl acrylate and 2-phenylethylmethacrylate or (ii) ethyl acrylate, ethyl methacrylate and trifluoroethylmethacrylate, wherein the lens has a shape and configuration of a toric lens.

2. The toric intraocular lens of claim 1 wherein the optic comprises a material that is substantially free of glistenings, has a refractive index of about 1.50 or greater, has a $T_g$ of about −20 to +25° C., and has an elongation of at least about 150%.

3. The toric intraocular lens of claim 1 wherein the Tack Quotient is about 1–3.

4. The toric intraocular lens of claim 3 wherein the Tack Quotient is about 1–2.

5. The toric intraocular lens of claim 4 wherein the Tack Quotient is about 1–1.5.

6. A toric intraocular lens comprising an optic consisting of a material that has a Tack Quotient of about 1 or greater, provided that said material does not consist essentially of (i) 2-phenylethyl acrylate and 2-phenylethylmethacrylate or (ii)

ethyl acrylate, ethyl methacrylate and trifluoroethylmethacrylate, wherein the lens has a shape and configuration of a toric lens.

7. A toric intraocular lens comprising a haptic consisting of a material that has a Tack Quotient of about 1 or greater, provided that said material does not consist essentially of (i) 2-phenylethyl acrylate and 2-phenylethylmethacrylate or (ii) ethyl acrylate, ethyl methacrylate and trifluoroethylmethacrylate, wherein the lens has a shape and configuration of a toric lens.

8. A toric intraocular lens comprising a haptic coated with a material that has a Tack Quotient of about 1 or greater, provided that said material does not consist essentially of (i) 2-phenylethyl acrylate and 2-phenylethylmethacrylate or (ii) ethyl acrylate, ethyl methacrylate and trifluoroethylmethacrylate, wherein the lens has a shape and configuration of a toric lens.

* * * * *